(12) United States Patent  
Viticoli et al.

(10) Patent No.: US 7,708,911 B2  
(45) Date of Patent: May 4, 2010

(54) TITANIUM OXIDE BASED HYBRID MATERIAL, RESPECTIVE PREPARATION PROCESS AND USES

(75) Inventors: Marco Viticoli, Rome (IT); Antonella Curulli, Rome (IT); Giuseppina Padeletti, Gubbio (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 308 days.

(21) Appl. No.: 11/662,775

(22) PCT Filed: Sep. 9, 2005

(86) PCT No.: PCT/EP2005/054486

§ 371 (c)(1),
(2), (4) Date: Feb. 25, 2008

(87) PCT Pub. No.: WO2006/027381

PCT Pub. Date: Mar. 16, 2006

(65) Prior Publication Data

US 2008/0258116 A1    Oct. 23, 2008

(30) Foreign Application Priority Data

Sep. 10, 2004    (IT)    .................. RM2004A0430

(51) Int. Cl.
| | |
|---|---|
| *H01B 1/08* | (2006.01) |
| *C23C 30/00* | (2006.01) |
| *C23C 16/30* | (2006.01) |
| *C23C 20/08* | (2006.01) |
| *G01N 27/28* | (2006.01) |

(52) U.S. Cl. .................. 252/520.22; 423/606; 600/372; 600/547

(58) Field of Classification Search ............ 252/520.22; 423/69, 608; 600/372, 547
See application file for complete search history.

(56) References Cited

U.S. PATENT DOCUMENTS 4,548,798 A * 10/1985 Rice .......................... 423/263

FOREIGN PATENT DOCUMENTS

WO    2005098074 A1    10/2005

OTHER PUBLICATIONS

Pavlov et al "Thermodynamic sharacteristics of hydrogen dissolution in cubic (sodium chloride type) titanium oxycarbides", Zhurnal Fizicheskoi Khimii (1979), 53(5), 1347 (Abstract Only).*
Pavlov et al "Thermal Stability of the cubic phase of TiCxOyHm", Zhurnal Fizicheskoi Khimii (1976), 50(8), 2127-8 (Abstract only).*
Perelyaev et al "Magnetic susceptibility of cubic phases of TiCxOy and TiCxOyHm", Izvestiya Akademii Nauk SSSR, Neorganicheskie Materialy (1978), 14(8), 1446-8 (Abstract Only).*

(Continued)

*Primary Examiner*—Mark Kopec
(74) *Attorney, Agent, or Firm*—Abelaman, Frayne & Schwab

(57) ABSTRACT

Titanium oxide based hybrid material usable as an electrochemical sensor which is particularly sensitive for detecting chemical and biological substances, in particular substances which act as neurotransmitters. Said material is represented by the formula: $TiC_xO_yH_z$ with $0.1 \leq x \leq 0.6$, $2.0 \leq y \leq 3.0$ and $0.1 \leq z \leq 0.9$. Said hybrid material is produced and deposited on a substrate using either a polymeric precursor route or MOCVD.

21 Claims, 1 Drawing Sheet

OTHER PUBLICATIONS

XP-002370869—Paik-Kyun Shin—The pH sensing and light-induced drift properties of titanium dioxide thin films deposited by MOCVD—Applied Surface Science 214 (2003) 214-221.

XP-000549649—Masato Kakihana—Invited Review "Sol-Gel" Preparation of High Temperature Superconducting Oxides—Journal of Sol-Gel Science and Technology 6, 7-55 (1996).

XP-001123858—Koktysh et al—Biomaterials by Design: Layer-By-Layer Assembled Ion-Selective and Biocompatible Films of $TiO_2$ Nanoshells for Neurochemical Monitoring—Adv. Funct. Mater. 2002, 12, No. 4, April.

XP-002370871—Yaev et al—"Magnetic susceptibility of cubic phases of $TiC_xO_y$ and $TiC_xO_yH_m$"—Database CA [Online] Chemical Abstracts Service, Columbus, Ohio, US—1978.

* cited by examiner

TITANIUM OXIDE BASED HYBRID MATERIAL, RESPECTIVE PREPARATION PROCESS AND USES

FIELD OF THE INVENTION

The present invention relates to a titanium oxide based hybrid material, the respective preparation process and its uses, in particular as a biosensor and electrochemical sensor. Said hybrid material will also be indicated below as TiCOHM (Titanium Carbonium Oxide Hybrid Material).

PRIOR ART

In the last decades, innovative materials in the form of thin film have been the object of intense research activity especially in sectors such as microelectronics and sensor devices, which had to satisfy the pressing requests for the miniaturisation of devices. Moreover, the development of numerous synthesis methods provided the growth of several thin films with different chemical compositions and structures, characterised by unique properties in comparison to bulk materials. Moreover, the dominant role of the surfaces and the possibility of controlling and modulating their characteristics, has extended the fields of application of thin films. In particular, in recent years great interest was directed to the development of biomaterials (materials designed to interface with biological systems to assess, treat, increase or replace any tissue, organ or function of the body) and materials for applications in the field of sensors, fuel cells and integrated circuits. In particular, the development of suitable materials for producing selective amperometric sensors for biological and not biological substances is still very open, as the devices applied at present in clinical diagnostics, in environmental analyses, and in forensic analyses, are not yet satisfactory in terms of selectivity and sensitivity. In fact, the discovery of a material able to provide the in vivo monitoring of neurotransmitters (important substances for the cerebral metabolism) level in brain would allow fundamental data to be obtained on the alterations of cerebral functionality in certain degenerative disease, such as Parkinson's disease and Alzheimer's disease. For such applications, different $TiO_2$ based hybrid materials have been developed and studied. However, these materials are applied only as membranes for immobilising enzymes and/or metalloproteins on glassy carbon electrodes (which represent the sector's detecting reference material), while they are not able to detect directly the presence of chemical and biological substances, such as enzymes and neurotransmitters, as they do not present a direct electrochemical activity with respect to those substances (Zhang Y. et al, *Electrochimica Acta*, vol. 49, p. 1981 (2004); Jiuhong Y. et al., *Analytical Chemistry*, vol. 74. p. 3579 (2002); Chen X. et al, *Biosensors and Bioelectronics*, vol 18, p. 999 (2003). An important aspect is the functionalisation and immobilisation of biological substances, such as enzymes, antibodies, or metalloproteins on the surfaces of materials. Various types of immobilisation are still used today, such as physical adsorption, chemical binding, ionic adsorption and the formation of self-assembled molecules on surfaces. The various types of immobilisation and functionalisation of surfaces show different advantages and drawbacks and the choice of one particular type of immobilisation rather than another has important applicative implications.

SUMMARY OF THE INVENTION

A titanium oxide based hybrid material (TiCOHM), has now been found and is the object of the present invention. This material may be used advantageously as an electrochemical sensor for the selective detection of chemical and biological substances, in particular substances which act as neurotransmitters; this hybrid material may also be used advantageously to immobilise enzymes, such as for example Glucose Oxidase and Horse Radish Peroxydase, and to functionalise surfaces for a broad spectrum of applications. Said material may be represented by means of the following formula: $TiC_xO_yH_z$ with $0.1 \leq x \leq 0.6$, $2.0 \leq y \leq 3.0$ and $0.1 \leq z \leq 0.9$.

Another object of the invention is the process for obtaining the TiCOHM with two techniques named Polymeric precursor route and MOCVD (Metalorganic Chemical Vapour Deposition).

Yet another object of the invention is the manufacturing of products that comprise the TiCOHM in the form of a surface layer for applications in the field of chemical sensors, biosensors, sensors for neurotransmitters, microelectronics, biomaterials. The TiCOHM may be coated on conductive, non conductive and semi-conductive supports, for example Pt, Au, Ag, Si, inert non metallic materials (that is which do not react with the reagents during deposition of the coating) in general among others TEFLON®, sintered alumina), in particular plastic materials that resist temperatures $\geq 300°$ C.

Another object of the invention is a composite material comprising at least one support material chosen among conductive, non conductive and semi-conductive materials resisting temperatures $\geq 300°$ C. coated with at least one layer of the hybrid material according to the invention.

A further object of the invention is products comprising one or more layers of the hybrid material according to the invention.

Other objects will be clear from the detailed description of the invention.

DETAILED DESCRIPTION OF THE INVENTION

Figure 1:
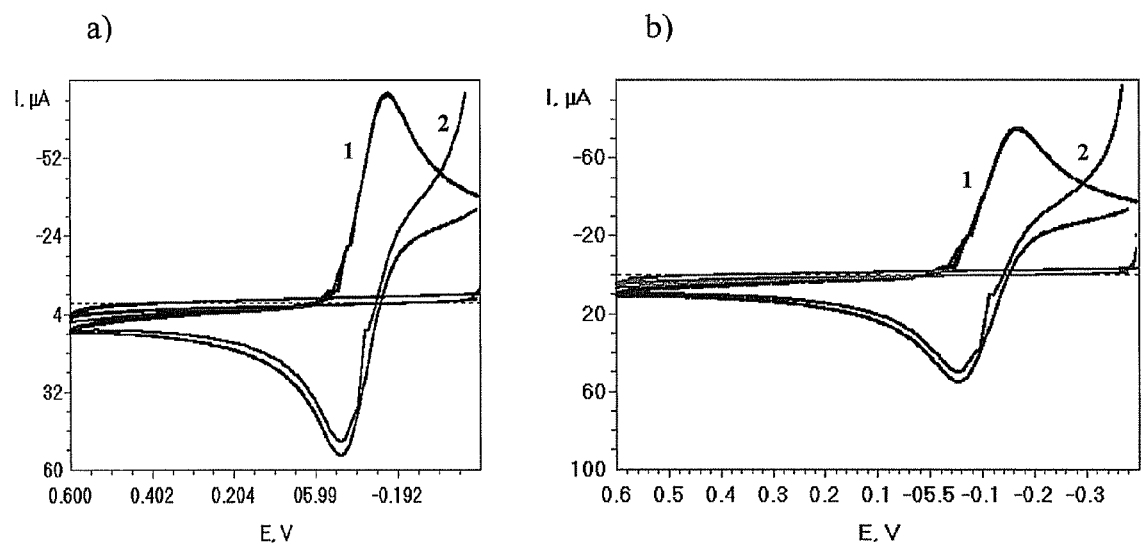
FIG. 1. Cyclic voltammetry of $[Fe(CN)_6]^{3-}$ 1mM in a buffer solution of phosphate 0.1M at pH 7.0 (curve 1) and at pH 2.0 (curve 2), carried out with a TiCOHM electrode obtained by a) polymeric precursor route and b) MOCVD. The flat curves were obtained at pH 11.

To produce the hybrid material (as will be explained better below, the term "hybrid" according to the invention means a material composed of an inorganic part and an organic one) two different methods of synthesis were used, a chemical synthesis, performed in an organic solution and based on the polymeric precursor route (Kakihana M. et al, *Journal of Sol-Gel Science and Technology*, vol. 6, pg 7 (1996)) and a gas phase synthesis, based on Metalorganic Chemical Vapour Deposition (MOCVD) (M. de Keijser et al., in Ferroelectric Thin Films: Synthesis and Basic Properties, edited by C. Paz de Arujo, J. F Scott, G. W. Taylor).

Polymeric precursor route: this method comprises the step of preparing a polymeric precursor containing titanium, and subsequently depositing the precursor on a special support with the Spin coating technique. As shown by all the chemical reactions listed below and concerning a preferred example of the invention, the synthesis process comprises the stages of: (i) formation of an organic acid - titanium alkoxide complex by the reaction at room T of a metalorganic precursor of Titanium with an organic, preferably aliphatic acid having two —COOH groups, particularly preferred is citric acid, in an alcohol solution, preferably ethylene glycol, for about 1 h. The metalorganic precursor may be Butyl Orthotitanate or Titanium Isopropoxide, or any titanium alkoxide, with a general formula $Ti(OR)_4$, where R is an alkyl radical with general formula $C_nH_{2n+1}$ with n preferably between 1 and 4. (ii) The complex is subsequently stabilised by means of a polyesterification reaction, brought about at a T between 100 and 120° C. (with times of about 10-15 minutes) in the presence of a polyfunctional alcohol, preferably ethylene glycol, and of an excess of organic acid, preferably citric acid.

compounds of the material to be deposited, with other gases, to produce a non volatile solid which is deposited on a substrate or support (metal and non metal, anyway resistant to the temperatures used during deposition) (Padaletti et al., Appl. Phys. A (2002)). In the present invention the volatile compound is generally a metalorganic precursor of Titanium (for example Titanium Isopropoxide, or any titanium alkoxide, with a general formula $Ti(OR)_4$, where R is an alkyl radical with general formula $C_nH_{2+1}$ with n preferably between 1 and 4 (including extreme values), which is introduced, by means of inert carrier gas (generally nitrogen or argon), in a high vacuum chamber, in which it is made to flow with different flow rates (between 2 and 10 standard cubic centimeters/minute (sccm)) on the support to be treated, heated to a temperature between 300 and 600° C. for times between 5 and

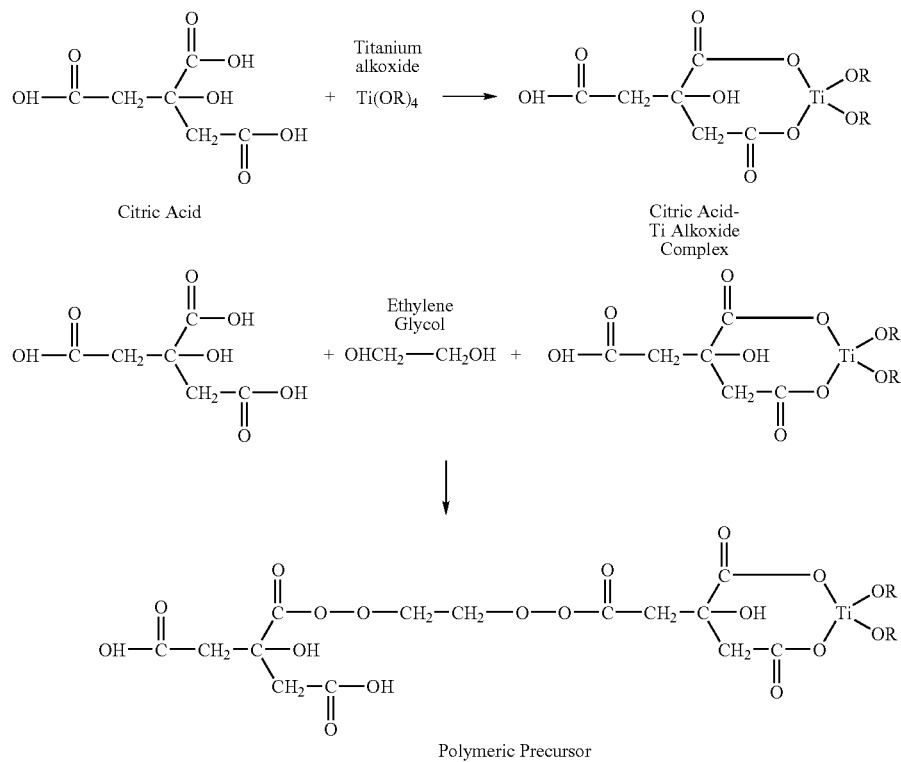

(iii) The polymeric precursor of Titanium thus obtained is deposited on a substrate or support (metal and non metal, anyway resistant to the temperatures used during deposition) with a spin coating technique (D. E. Bornside et al., *Journal of Imaging Technology*, Volume 13 pg 122 (1987)). This techniques consists in applying the polymeric precursor on a support which is rotated at variable speeds (between 2000 and 9000 rpm) and times (between 30 and 90 seconds). This obtains a layer uniformly distributed on the support which is then subjected to heat treatment at a T between 300 and 400° C. for about 10-15 minutes. The titanium oxide based hybrid material (TiCOHM) is thus obtained, in form of a thin layer (thickness variable from 50 to 250 nm) that adheres perfectly to the support. This material is defined as hybrid because it is characterised by an inorganic part and an organic part, deriving from the incomplete pyrolysis of the polymeric precursor. Metalorganic Chemical Vapour Deposition (MOCVD): the technique comprises a reaction in gaseous phase of volatile 30 minutes. The contact with the heated support produces a partial decomposition of the titanium precursor, and the formation of the hybrid material (TiCOHM), which is presented as a thin layer (thickness between 20 and 300 nanometers) that adheres uniformly to the support.

By means of MOCVD and polymeric precursor route techniques it is possible to obtain TiCOHM coatings on metal supports (Platinum, Gold, Silicon, Palladium, Steel), on inert non metallic supports (Alumina, Teflon,) and on plastic materials resistant at least to T of 300° C.

The deposited hybrid material which is obtained with both techniques may be represented by the general formula $TiC_xO_yH_z$ with $0.1 \leq x \leq 0.6$, $2.0 \leq y \leq 3.0$ and $0.1 \leq z \leq 0.9$. It is a nanostructured $TiO_2$ based hybrid material (that is composed of an organic part and of an inorganic part, with structural characteristics, such as thickness and grain size, measured in nanometers), but with a structure composed also of other functional groups bonded to the Titanium on the surface, principally OH groups and OR organic groups which represent the active sites of the material, in which the R groups are generally linear alkyl chains, with formula $C_nH_{2n+1}$ with $1 \leq n \leq 4$.

The TiCOHM films obtained with the two different deposition methods are characterised by a high degree of uniformity. The surface of the films is characterised by a fine granular microstructure (mean grain dimensions preferably between 20 and 50 nm) and by low roughness values (mean roughness between 0.2 and 2 nm depending on the support used).

This material, called Titanium Carbonium Oxide Hybrid Material (TiCOHM) shows a functionalised surface, able to act either as an electrochemical sensor of organic and inorganic substances, or as a biosensor, or as an amperometric sensor for detecting neurotransmitters in the presence of interferents, and demonstrates an excellent electrochemical activity towards organic and inorganic probes (substances used for testing sensors, including caffeic acid and the [Fe$(CN)_6]^{3-}$, $Na_3IrCl_6 \cdot H_2O$, and $[Ru(NH_3)_6]^{3+}$ systems). Moreover it proved to be active as a biosensor, after the immobilisation on its surface of enzymes commonly used in sensoristics, such as Glucose Oxidase and Horse Radish Peroxydase. Lastly, TiCOHM is a completely innovative material, as it allows the determination of neurotransmitters in the cerebral liquids in the presence of physiological concentrations of ascorbate (for example between $5 \times 10^{-5}$ and $3 \times 10^{-4}$ mol/l), without any pre-treatment of its surface, and with extraordinary performances by the sensors produced (the sensors for testing TiCOHM may be realized by inserting the TiCOHM in a cylindrical container, electronically connected to a suitable appliance for measuring signal transduction, such as a system for computerised electrochemical measurements (e.g. AMEL 433)) in terms of stability, sensitivity and biocompatibility. On analysing the structure of the TiCOHM it was also found that, using this material, it is possible to determine the most important neurotransmitters with very low concentrations, down to 10 μM, selectively in the presence of ascorbic acid in a concentration of more than 3 times larger than that of the neurotransmitters. The use of TiCOHM would allow a significant step forward in the selective determination of neurotransmitters, eliminating the interference of electroactive ions with a negative charge (principally ascorbate and urate ions). The neurotransmitters that can be detected are for example dopamine, epinephrine and norepinephrine. The combination of selectivity and biocompatibility shown by the material of the invention is an essential requirement for the planning of long-term implantable devices and for monitoring the activity of neuronal cells. Therefore real time measurements with practical and sensitive electrochemical systems comprising the material of the invention may be extremely useful in the aetiology and therapy of disorders linked to the neurotransmitters.

TiCOHM possesses excellent characteristics for being applied in the field of sensoristics. In particular, excellent results have been obtained using TiCOHM films in chemical sensors, third generation biosensors in which the enzyme is immobilised directly on the material without the aid of membranes (as occurs in second generation biosensors), and sensors for determining neurotransmitters. This last application is particularly interesting, as the TiCOHM films obtained according to the present invention are a material particularly suited to determine the concentration of a neurotransmitter, for example Dopamine, in the presence of a high concentration of interfering species such as ascorbic acid. This characteristic would allow the material according to the invention to be immediately applied as an amperometric sensor for the determination in vivo of important neurotransmitters in the study of pathologies such as Parkinson's disease and Alzheimer's.

TiCOHM could also be applied in microelectronics, as material with a high dielectric constant and, considering the high degree of nanostructuring and the large surface area of the TiCOHM films, in the catalysis sector.

The following examples illustrate the invention and are not to be considered as limiting its scope.

EXAMPLE 1

Synthesis of TiCOHM

Thin films of TiCOHM were produced by means of two different methods of synthesis:

1) Polymeric Precursor Route

TiCOHM films were obtained by means of the synthesis of a polymeric precursor of Titanium, and its subsequent deposition on (100) p-Silicon substrates of different shapes and dimensions (from min. 1×1 cm to max. 5×5 cm$^2$) with the Spin-Coating technique.

The polymeric precursor of Titanium was obtained with the following synthesis procedure. 16.8 g of Tetrabutyl Orthotitanate [Fluka >97%] were taken and transferred into a container; at this point 30 ml of Ethylene Glycol [Carlo Erba 95%] (EG) were added, stirring until a clear and transparent solution was formed. 20 g of Citric Acid (AC) were then added, stirring the solution for about 30'. A straw-yellow coloured solution was obtained, which was then subjected to thermal annealing at a T ~110-120° C. for 15', in such a way as to obtain a viscous gel which constitutes the polymeric precursor of Titanium. As is shown by the set of chemical reactions listed above, this method of synthesis contemplates the formation of a citric acid—metalorganic precursor complex and the subsequent formation of a polymeric precursor through the reaction of the citric acid—metalorganic precursor complex with Ethylene Glycol at a T of 110-120° C. The polymeric precursor thus prepared was diluted with isopropylic alcohol in a 1:1 ratio, and deposited by spin coating (Spin Coater SCS model P6708) at room temperature on (100) p-Si substrates of different shapes and dimensions (Lucent Technologies-Wacker Siltronic corp.), in the following experimental conditions: rpm=6500, acceleration=3000, t=90 s. Each layer thus deposited was subjected to annealing at 300-350° C., to provide the pyrolysis of the polymeric precursor. Multiple layers were deposited in order to obtain films with a different thickness, between 50 nm and 200 nm.

2) Metalorganic Chemical Vapour Deposition

TiCOHM films were also obtained using another deposition technique, metalorganic chemical vapour deposition (MOCVD). The deposition of TiCHOM films was carried out with a MOCVD apparatus, comprising a stainless steel cylindrical reaction chamber, able to reach a vacuum of about $10^{-9}$ Torr in the pre-deposition phase. The deposition of TiCHOM films was carried out using Titanium (IV) Isopropoxide [CHEMAT TECHNOLOGY 97%] as a precursor of Ti, oxygen ($O_2$) and nitrogen ($N_2$) as reactive gas and carrier gas respectively. The vapours of Ti (IV) Isopropoxide were made flow into the reaction chamber through the carrier gas. Oxygen was dynamically introduced in the chamber (that is through a continuous incoming flow of Oxygen) during deposition, while the temperature of the substrate of p-Si (100) (Lucent Technologies-Wacker Siltronic corp.) was kept constant at $T_s$=600° C. The deposition conditions of the TiCOHM films are summed up in table 1.

TABLE 1

Condition of TiCOHM deposition by means of MOCVD.

| Precursor | T precursor (° C.) | Flow $N_2$ (sccm) | Flow $O_2$ (sccm) | T substrate (° C.) | P deposition (Torr) |
|---|---|---|---|---|---|
| Ti (IV) isopropoxide | 25 | 5 | 20 | 600 | 2 |

(sccm means standard cubic centimetres/minute)

EXAMPLE 2

Chemical and Physical Characteristics of TiCOHM

The chemical and physical characteristics of TiCOHM were analysed with different characterisation techniques. The morphology and microstructure of the TiCOHM films were analysed by Atomic Force Microscopy (AFM). The AFM analyses were carried out in air with a Digital Instruments microscope, model Dimension 3100. Topographic images were obtained by analysing areas with different dimensions, from 500×500 $nm^2$ to 10×10 micron 2. The surfaces were characterised with the following parameters: $Z_r$=vertical excursion between the highest point and the lowest on the fraction of surface analysed, $R_a$=mean roughness, with reference to an imaginary central plane, and $R_{rms}$=standard deviation of the values of Z within the area analysed.

The AFM analyses carried out on TiCOHM films obtained by MOCVD and polymeric precursor route revealed the growth of nanostructured films, uniformly covering the Silicon substrate. The surface of the films is characterised by a fine granular microstructure (mean grain dimensions=20-30 nm) and, as shown in table 2, by low roughness values, similar to those of the silicon substrate.

TABLE 2

Roughness parameters of the Silicon and of the TiCOHM films deposited using different techniques.

| Sample | Deposition technique | Substrate Temp. (° C.) | Zr (nm) | Ra (nm) | Rq (nm) |
|---|---|---|---|---|---|
| $SiO_2$/p-Si (100) | — | — | 3.909 | 0.204 | 0.266 |
| a) TiCOHM | Polymeric precursor route | ≦350° C. | 3.393 | 0.276 | 0.351 |
| b) TiCOHM | MOCVD | 600° C. | 2.287 | 0.207 | 0.259 |

The chemical composition of TiCOHM films was analysed by X-ray photoelectron spectroscopy (XPS). The measurements were carried out with a VG Escalab MKII spectrometer, using a non monochromatised source of AlKα(1486.6 eV). For the determination of the chemical species present, the XPS spectrums were registered in the interval of Binding Energies (B.E.) between 0 and 600 eV. The XPS analyses carried out on the sample produced according to the method in point 1) showed the presence of Ti, C and O on the surface and inside the films, as indicated by the presence of the signals Ti 2p (459 eV) C 1s (285 eV) and O 1s (531 eV). Moreover, from the deconvolution of the $C_1s$ and of O 1s signals, it has been observed that there are various functional groups on the surface. In particular, the C is signal observed in TiCOHM films is made up of 3 different components. The peaks with the highest energy, respectively C1 (286.5 eV) and C2 (289.0 eV), are due to the presence of C atoms respectively bonded to the Ti—Si network through the oxygen ($SiO_2$/Ti)—O—C and of C atoms which form double bonds with the Oxygen, probably due to the presence of $CO_2$ absorbed on the surface of the films, as may be seen also from the FT-IR spectrums. The peak at 284.9 eV indicates the presence of aliphatic C, partly due to contamination following the contact of the sample with the external environment, and partly to the presence of aliphatic chains in the films, due to the incomplete pyrolysis of the polymeric precursor.

The spectrum of O 1s correlates well with that of C1s. In the spectrum of O 1s, two components are shown: the component with the lower energy, O1 at 530.6 eV, corresponding to Oxygen atoms bonded to Ti to form the oxide $TiO_2$, and the peak at 532.2 eV, due to the presence of OH groups on the surface bonded to Ti and to C—O organic bonds, derived from ethylene glycol.

The TiCOHM films obtained by MOCVD show similar characteristics to those obtained with the polymeric precursor route. In these films the presence of aliphatic organic groups and of OH groups has been observed on the surface, too. The signal of O 1s is made up of three components, the one with the highest energy may be attributed to the presence of $CO_2$ and $H_2O$ adsorbed on the surface.

The chemical composition (expressed in % at.), obtained integrating the areas of the signals of C1s, Ti 2p and O1s, may be substantially reproduced for the TiCOHM films obtained with the two different methods, considering that the experimental error for XPS analysis is about ±10%.

TABLE 3

Chemical composition (% at.) of the TiCOHM films obtained with the different deposition techniques.

| Chemical element | Polymeric precursor TiCOHM (at %) | MOCVD TiCOHM (at %) |
|---|---|---|
| C 1s | 8 | 12 |
| Ti 2p | 27 | 22 |
| O 1s | 65 | 66 |

EXAMPLE 3

Electrochemical Tests

The electrochemical tests were carried out using cyclic voltammetry and differential voltammetry techniques with particularly sensitive impulses in the case of the determination of substances of biological interest.

The system was explored in a potential range between −400 e+600 mV using a Ag/AgCl reference electrode, and all the measurements were taken using a computerised electrochemical measurement system AMEL 433.

In so far as regards the use of TiCOHM as a chemical sensor, the new material was characterised by comparing its behaviour with that of a commercial glassy carbon electrode. The electro-activity of TiCOHM was assessed using classical electrochemical reference systems, such as $[Fe(CN)_6]^{3-}$, $Na_3IrCl_6 \cdot H_2O$, and $[Ru(NH_3)_6]^{3+}$. As may be observed in FIG. 1, the voltammograms carried out with the above-mentioned inorganic probes are characterised by two distinct redox peaks, indicating a reversible behaviour of the sensor and the absence of absorption of chemical substances on the electrode. As shown in table 4, the values of anodic ($E_{pa}$) and cathodic ($E_{pc}$) potential are similar to those obtained with the commercial glassy carbon electrode, while the intensity of the anodic ($I_{pa}$) and cathodic ($I_{pc}$) peaks is considerably higher when TiCOHM is used, indicating a greater sensor sensitivity.

TABLE 4

Data of the cyclic voltammetries carried out on different redox systems, using TiCOHM and the commercial glassy carbon electrode.

| Probe | $E_{pa}$(mV) TiCOHM | $E_{pa}$(mV) Glassy Carbon | $E_{pc}$(mV) TiCOHM | $E_{pc}$(mV) Glassy Carbon | microE$_p$(mV) TiCOHM | microE$_p$(mV) Glassy Carbon | $I_{pa}$(microA) TiCOHM | $I_{pa}$(microA) Glassy Carbon | $I_{pc}$(microA) TiCOHM | $I_{pc}$(microA) Glassy Carbon |
|---|---|---|---|---|---|---|---|---|---|---|
| Fe(CN)$_6^{3-}$ 1 mM | 280.0 | 280.0 | 220.0 | 200.0 | 60.0 | 80.0 | 60.0 | 9.0 | −60.5 | −8.5 |
| Na$_3$IrCl$_6$·H$_2$O 1 mM | 700.0 | 710.0 | −542.0 | −543.2 | 158.0 | 166.8 | 32.0 | 11.5 | −29.5 | −10.5 |
| Ru(NH$_3$)$_6$ 1 mM | −300.0 | −310.0 | −380.0 | −398.0 | 80.0 | 88.0 | 11.0 | 8.0 | −12.0 | −6.5 |

Figure 2:
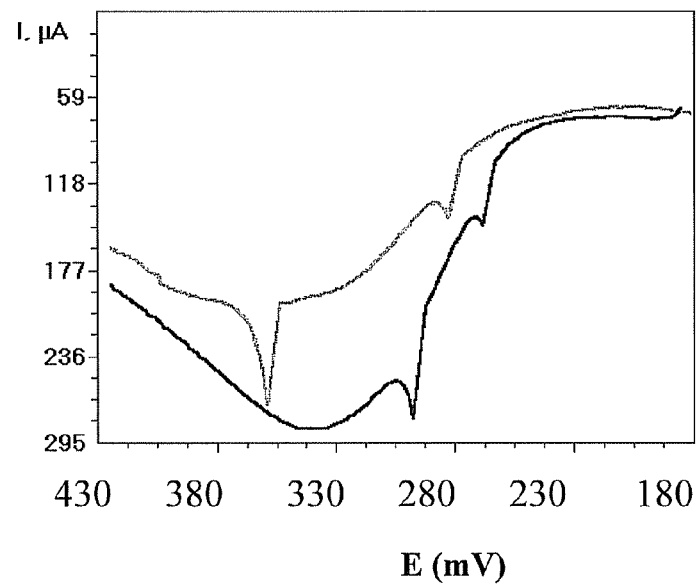
FIG. 2. Determination by means of DPV of dopamine in the presence of Ascorbic Acid: blue curve (curve 1), dopamine 0.01 μM in the presence of ascorbic acid 0.0ĩ μM; red curve (curve 2), dopamine 0.0ĩ microM in the presence of ascorbic acid 0.0ĩ mM̃.

The electrochemical tests carried out revealed an excellent response of TiCOHM for the detection of certain substances of biological interest, such as neurotransmitters like Dopamine, Epinephrine and Norepinephrine. In particular, TiCOHM proved to be a particularly innovative material, as it allowed the determination of Dopamine in the presence of Ascorbic Acid. The measurements were taken with cyclic voltammetry and impulse differential voltammetry, to detect substances present in very low concentrations. As may be seen in FIG. 2, the use of TiCOHM allows the selective determination of dopamine in concentrations of 0.01 µM in the presence of different concentrations of ascorbic acid. The determination was carried out by impulse differential voltammetry in a potential range between +0.100 mV and +400 mV. The potential for ascorbic acid is +380 mV and that of dopamine is +280 mV. The blue line refers to the determination of dopamine 0.01 µM in the presence of ascorbic acid 0.01 µM while the red curve refers to the determination of the same concentration of dopamine in the presence of ascorbic acid.

Moreover a high stability of TiCOHM was found both in the electrochemical tests and in the determination of neurotransmitters. As may be seen from the data given in table 5, after more than 70 days the determination system is still functioning and the electrochemical signal is decreased by only 40%. This result is extremely important in terms of reliability and resistance of TiCOHM if we consider that the materials used up till now for determining neurotransmitters present, with the same performance, an operative stability of 7 days at the most. In the case of the other neurotransmitters, the limit of detection obtained was 0.2 µM both for epinephrine and for norepinephrine.

Lastly, the possibility of application of TiCOHM films as biosensors was assessed. In particular, two enzymes, glucose oxidase and horse radish peroxydase, were immobilised on TiCOHM films and their electrochemical behaviour was assessed, always in physiological pH conditions, comparing the data with commercial electronic material. The method of immobilisation for enzymes is the traditional one (Manowitz P. et al., *Biosensors & Bioelectronics*, vol. 10 pg 359 (1995)), which involves the use of glutaraldehyde as crosslinking system together with BSA (Bovine Serum Albumine) as homogenising system: the enzyme remains trapped in the "mesh" of glutaraldehyde with a biological surrounding due to BSA. The results obtained were extremely interesting, as direct communication was observed between the TiCOHM and the active site of the enzyme. This allowed preliminary measurements to be made for the production of third generation biosensors, with satisfactory results in the case of both peroxydase and glucose oxidase, since it was possible to carry out calibrations of the glucose and of the $H_2O_2$ with detection limits of around 20 µM and with stability for the enzymes immobilised with glutaraldehyde and BSA.

The invention claimed is:

1. Titanium oxide based hybrid material represented with the following formula: TiC$_x$O$_x$H$_z$ with 0.1≦x≦0.6, 2.0≦y≦3.0 and 0.1≦z≦0.9, wherein said titanium oxide based hybrid material is in the form of a film having aliphatic groups and/or OH groups on the surface thereof.

2. Process for obtaining the hybrid material according to claim 1 comprising the steps of:
   (i) formation of an organic acid-titanium alkoxide complex by the reaction at room temperature of a metalorganic precursor of titanium with an organic acid in an alcohol solution for about 1 h, where the metalorganic precursor is selected from the group consisting of butyl orthotitan-

TABLE 5

Long-term stability of the chemical sensor with regard to neurotransmitters. TiCOHM films obtained using different deposition techniques present the same performances.

| | Electrodes | | | | | | | |
|---|---|---|---|---|---|---|---|---|
| Signal | Day 1 $I_{p100}$ (%) | Day 2 $I_{pc}/I_{p100}$ (%) | Day 7 $I_{pc}/I_{p100}$ (%) | Day 14 $I_{pc}/I_{p100}$ (%) | Day 21 $I_{pc}/I_{p100}$ (%) | Day 30 $I_{pc}/I_{p100}$ (%) | Day 60 $I_{pc}/I_{p100}$ (%) | Day 70 $I_{pc}/I_{p100}$ (%) |
| TiCOHM (polymeric precursor route) | 100 | 100 | 100 | 90 | 90 | 85 | 85 | 60 |
| TiCOHM (MOCVD) | 100 | 100 | 95 | 90 | 90 | 85 | 85 | 60 | ate, titanium isopropoxide, or a titanium alkoxide of the general formula Ti(OR)$_4$, where R is an alkyl radical with general formula C$_n$H$_{2n+1}$ with n ranging from 1 and 4;

(ii) stabilizing of the complex by means of a polyesterification reaction, brought at a temperature of about between 100 and 120° C., for times of about 10-15 minutes, in the presence of a polyfunctional alcohol and of an excess of organic acid; and (iii) deposition of said polymeric precursor of titanium on a substrate or support with a spin coating technique.

3. Process according to claim 2 wherein the spin coating comprises the stage of applying the polymeric precursor on the substrate or support which is rotated at variable speeds between 2000 and 9000 rpm and for times between 30 and 90 seconds, the layer thus applied being subjected to heat treatment at a T between 300 and 400° C. for about 10-15 minutes.

4. Process according to claim 2 wherein the support is a metal support selected from the group consisting of Platinum, Gold, Silicon, Palladium and Steel.

5. Process according to claim 2 wherein said substrate or support is a non metal support selected from the group consisting of alumina and plastic materials.

6. Process for obtaining the hybrid material according to claim 1 comprising the step of a reaction in gaseous phase of volatile compounds of the material to be deposited, with other gases, to produce a non volatile solid which is deposited on a substrate or support resistant to temperatures ≦300° C., where the volatile compound is selected from the group consisting of metalorganic precursor of titanium; said deposition being performed by introducing the volatile compound, by means of inert carrier gas, in a high vacuum chamber, in which it is made to flew with different flow rates between 2 and 10 standard cubic centimeters/minute on the substrate or support to be treated, heated to a temperature between 300 and 600° C. for times between 5 and 30 minutes, said contact with the heated substrate or support producing a partial decomposition of the titanium precursor, and the formation of the hybrid material according to claim 1.

7. Electrochemical sensor made of the material according to claim 1.

8. Amperometric sensor made of a material according to claim 1.

9. Amperometric sensor according to claim 8 for the determination in vivo of neurotransmitters.

10. Composite material comprising at least one support material selected from the group consisting of conductive, non conductive and semi-conductive supports resistant to temperatures ≦300° C. bearing at least one layer of hybrid material according to claim 1.

11. Composite according to claim 10 wherein the support material is a metal support selected from the group consisting of Platinum, Gold, Silicon, Palladium, and Steel.

12. Composite according to claim 10 wherein said substrate or support is a non metal support selected from the group consisting of alumina and plastic materials.

13. Composite according to claim 10 wherein the hybrid material is in the form of a thin layer with thickness between 20 and 300 nanometers.

14. Composite according to claim 10 wherein the hybrid material is in the form of a thin layer with thickness between 50 and 250 nanometers.

15. Composite according to claim 10 wherein the hybrid material is in form of a layer characterised by a fine granular microstructure with mean grain dimensions between 20 and 50 nm and mean roughness values between 0.2 and 2 nm.

16. Manufactured items comprising at least one composite material according to claim 10.

17. Biosensor made of the material according to claim 1.

18. A sensor made from the material according to claim 1, wherein said sensor is used in the detection of neurotransmitters.

19. Sensor according to claim 18, wherein the neurotransmitter is selected from the group consisting of dopamine, epinephrine, and norepinephrine.

20. Implantable device suited to monitor the activity of neuronal cells made of the material according to claim 1.

21. Manufactured items comprising one or more layers of the hybrid material according to claim 1.

* * * * *